United States Patent
Reed (10) Patent No.: US 9,534,215 B2
(45) Date of Patent: Jan. 3, 2017

(54) SYSTEMS AND METHODS FOR SUBSTRATE ENRICHMENT

(71) Applicant: LIFE TECHNOLOGIES CORPORATION, Carlsbad, CA (US)

(72) Inventor: Brian Reed, Woodbridge, CT (US)

(73) Assignee: Life Technologies Corporation, Carlsbad, CA (US)

(*) Notice: Subject to any disclaimer, the term of this patent is extended or adjusted under 35 U.S.C. 154(b) by 0 days.

(21) Appl. No.: 14/736,734

(22) Filed: Jun. 11, 2015

(65) Prior Publication Data

US 2015/0361418 A1 Dec. 17, 2015

Related U.S. Application Data

(60) Provisional application No. 62/010,573, filed on Jun. 11, 2014.

(51) Int. Cl.
*C07H 1/06* (2006.01)
*C12N 15/10* (2006.01)
*C12Q 1/68* (2006.01)

(52) U.S. Cl.
CPC ......... *C12N 15/1013* (2013.01); *C12Q 1/6806* (2013.01); *C12Q 1/6844* (2013.01); *C07H 1/06* (2013.01)

(58) Field of Classification Search
None
See application file for complete search history.

(56) References Cited

U.S. PATENT DOCUMENTS

| | | | |
|---|---|---|---|
| 3,258,453 A | 6/1966 | Chi et al. | |
| 5,055,408 A | 10/1991 | Higo et al. | |
| 5,647,994 A | 7/1997 | Tuunanen et al. | |
| 6,033,574 A | 3/2000 | Siddiqi et al. | |
| 6,413,780 B1 | 7/2002 | Bach et al. | |
| 7,842,457 B2 * | 11/2010 | Berka | B01L 3/502707 435/6.16 |
| 8,025,788 B2 | 9/2011 | Cardosi et al. | |
| 8,562,920 B2 | 10/2013 | Tajima | |
| 2005/0013741 A1 | 1/2005 | a'Brassard | |
| 2005/0047963 A1 | 3/2005 | Safar et al. | |
| 2006/0211080 A1 | 9/2006 | Frost et al. | |
| 2007/0214900 A1 | 9/2007 | Porat et al. | |
| 2008/0003571 A1 | 1/2008 | McKernan et al. | |
| 2010/0137165 A1 | 6/2010 | Tajima | |
| 2011/0087016 A1 | 4/2011 | Suo | |
| 2013/0131053 A1 | 5/2013 | Nanchen et al. | |
| 2013/0164789 A1 | 6/2013 | Schultz et al. | |

FOREIGN PATENT DOCUMENTS

| | | |
|---|---|---|
| EP | 2333560 | 6/2011 |
| WO | 2005/082098 | 9/2005 |
| WO | 2007/086935 | 8/2007 |
| WO | 2007/149432 | 12/2007 |
| WO | 2008/052138 | 5/2008 |
| WO | 2010/051975 | 5/2010 |
| WO | 2012036679 | 3/2012 |
| WO | 2012/138926 | 10/2012 |
| WO | 2013/010062 | 1/2013 |
| WO | 2013/016459 | 1/2013 |
| WO | 2014/068407 | 5/2014 |

OTHER PUBLICATIONS

Liu et al. science (2006), vol. 313, pp. 958-960.*
International Search Report and Written Opinion of the International Searching Authority for International Application No. PCT/US2015/035366 mailed Aug. 18, 2015, 11 pages.
Chunsun, Zhang et al., "Single-Molecule DNA Amplification and Analysis Using Microfluidics", *CHem. Rev.* vol. 110, 2010, pp. 4910-4947.

* cited by examiner

*Primary Examiner* — Patrick Lewis (57) ABSTRACT

A method of separating bead substrates includes applying an emulsion to an emulsion-breaking solution. A dispersed phase of the emulsion includes an unbound polynucleotide, a first set of bead substrates and a second set of bead substrates. The unbound polynucleotide includes a segment complementary to a coupling oligonucleotide. The first set of bead substrates includes the coupling oligonucleotide extended to include a segment complementary to a portion of the unbound polynucleotide. The second set of bead substrates includes the coupling oligonucleotide. The emulsion-breaking solution includes an interference probe having a sequence similar to the coupling oligonucleotide or complementary to the coupling oligonucleotide. The method further includes binding beads of the first set of bead substrates to separation substrates and separating unbound beads of the second set of bead substrates from the beads of the first set of bead substrates bound to the separation substrates.

19 Claims, 7 Drawing Sheets

SYSTEMS AND METHODS FOR SUBSTRATE ENRICHMENT

CROSS-REFERENCE TO RELATED APPLICATION(S)

This application claims benefit of U.S. Provisional Application No. 61/010,573, filed Jun. 11, 2014, which is incorporated herein by reference in its entirety.

FIELD OF THE DISCLOSURE

This disclosure, in general, relates to systems and methods for enriching substrates suspended in a dispersion.

BACKGROUND

As biological and chemical sciences advance, scientists increasingly turn to separation techniques to isolate and analyze analytes. In particular, the chemical sciences are turning to enrichment methods to isolate and analyze ever smaller concentrations of compounds. In the biological sciences, scientists seek to isolate and analyze increasingly complex molecules, such as DNA, RNA, and proteins, such as enzymes.

In particular, compounds can be bound to dispersed substrates, such as particles or beads, and then isolated for analysis. In an example, a substrate bound to compounds can be applied to a sensor for analysis. In another example, the compounds can be separated from the substrates following isolation and can be analyzed separately. Such isolated substrates bound to compounds or analytes can be used for detecting trace amounts of chemical agents, biologically active reagents, or can be used in analyzing molecules, such as DNA or RNA. In particular, such dispersed substrates bound to polynucleotides or proteins can be used for sequencing.

SUMMARY

In an exemplary embodiment, amplified substrates are conjugated with copies of a target sequence through emulsion amplification. The emulsion is applied over a breaking solution that includes interference probes that limit binding of unbound template polynucleotides to unamplified substrates that lack conjugation to the copies of the target sequence. The amplified substrates are separated from the unamplified substrates, thus enriching the amplified substrates. The enriched amplified substrates can be loaded onto biosensors.

BRIEF DESCRIPTION OF THE DRAWINGS

The present disclosure may be better understood, and its numerous features and advantages made apparent to those skilled in the art by referencing the accompanying drawings.

DESCRIPTION OF THE PREFERRED EMBODIMENT(S)

In an exemplary embodiment, substrates, such as bead or particle substrates, are amplified to include multiple copies of target polynucleotides using an emulsion. Herein, amplified substrates are substrates to which copies of a target polynucleotide are attached. For example, an amplification reaction can extend primers conjugated to the substrate. Such primers are referred to herein as coupling oligonucleotides or coupling sites. Following amplification, the emulsion can be applied over a breaking solution that includes interference probes to prevent amplification byproducts from binding to unamplified substrates. Amplified substrates are separated from the unamplified substrates, and the amplified substrates are loaded onto a biosensor. The biosensor loaded with the amplified substrates can be used to sequence the target polynucleotides or perform other testing. The amplification reaction can utilize polymerase chain reaction (PCR) or can utilize recombinase polymerase amplification (RPA). In an example, the interference probe is complementary to a coupling oligonucleotide coupled to the substrates. In another example, the interference probe has the same sequence as the coupling oligonucleotide and can be complementary to a segment of an unbound template polynucleotide. In a particular example, amplified substrates can be bound to a magnetic substrate and the amplified substrates can be separated from unamplified substrates utilizing magnetic separation techniques.

Figure 1:
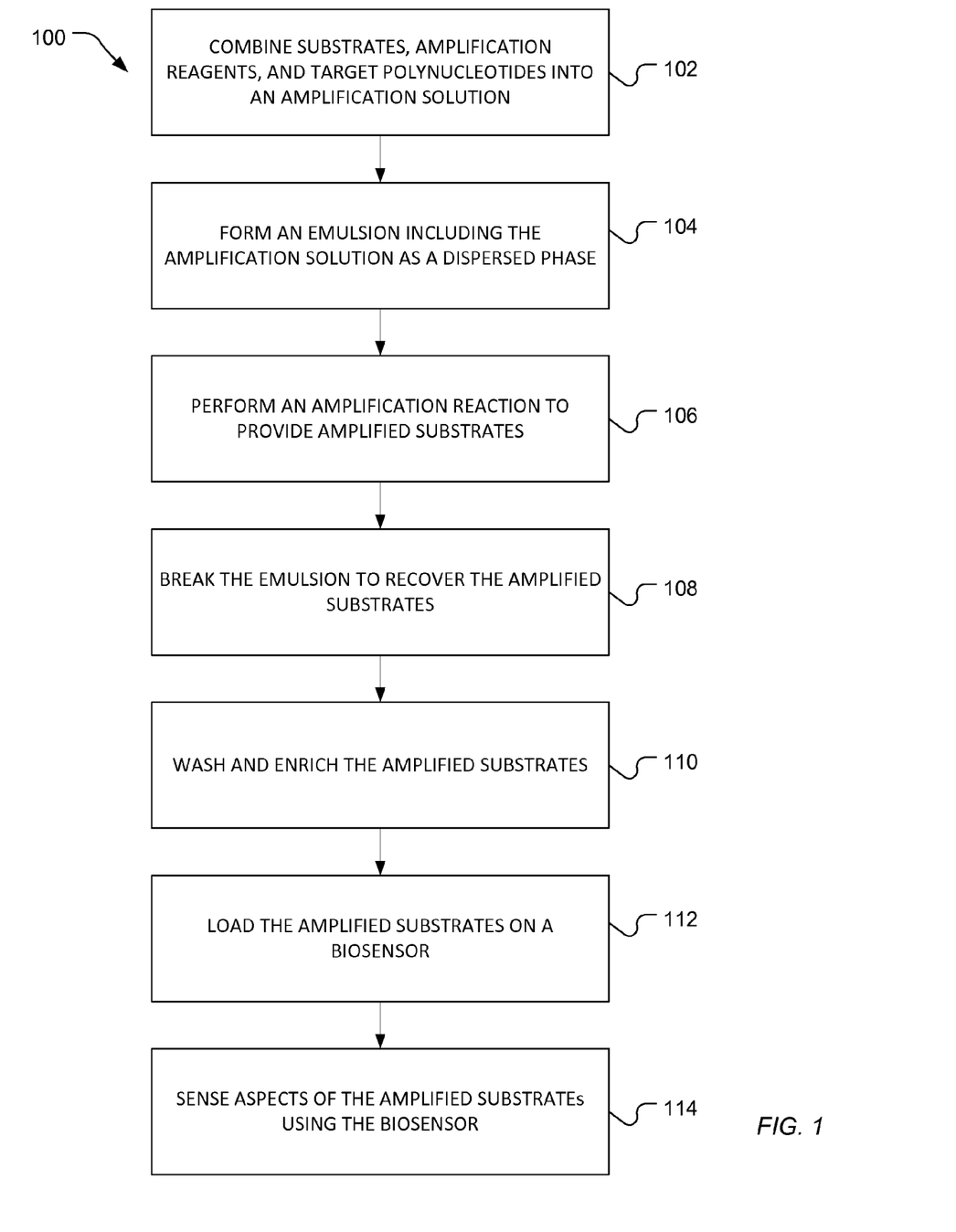
FIG. 1 includes a block flow diagram of an exemplary method for analyzing a target polynucleotide.

As illustrated in FIG. 1, a method 100 includes combining substrates, amplification reagents, and target polynucleotides into an amplification solution, as illustrated at 102. The substrates can include bead or particulate substrates. In particular, a substrate includes bead substrates formed of hydrophilic polymers. The substrates can carry a charge. Alternatively, the substrates can be neutral.

For example, substrates can be formed from monomers including a radically polymerizable monomer, such as a vinyl-based monomer. In an example, the monomer can include acrylamide, vinyl acetate, hydroxyalkylmethacrylate, or any combination thereof. In a particular example, the hydrophilic monomer is an acrylamide, such as an acrylamide including hydroxyl groups, amino groups, carboxyl groups, or a combination thereof. In an example, the hydrophilic monomer is an aminoalkyl acrylamide, an acrylamide functionalized with an amine terminated polypropylene glycol (D, illustrated below), an acrylopiperazine (C, illustrated below), or a combination thereof. In another example, the acrylamide can be a hydroxyalkyl acrylamide, such as hydroxyethyl acrylamide. In particular, the hydroxyalkyl acrylamide can include N-tris(hydroxymethyl)methyl)acrylamide (A, illustrated below), N-(hydroxymethyl)acrylamide (B, illustrated below), or a combination thereof. In a further example, a mixture of monomers, such as a mixture of hydroxyalkyl acrylamide and amine functionalize acrylamide or a mixture of acrylamide and amine functionalized acrylamide, can be used. In an example, the amine functionalize acrylamide can be included in a ratio of hydroxyalkyl acrylamide:amine functionalized acrylamide or acrylamide:amine functionalized acrylamide in a range of 100:1 to 1:1, such as a range of 100:1 to 2:1, a range of 50:1 to 3:1, a range of 50:1 to 5:1 or even a range of 50:1 to 10:1.

In a particular example, the substrates are hydrogel bead substrates.

Each of the substrates can include coupling sites to which a template polynucleotide can hybridize. For example, the coupling sites can each include a coupling oligonucleotide complementary to a section of a template polynucleotide. The template polynucleotide can include the target polynucleotide or segments complementary to the target polynucleotide, in addition to segments complementary to the coupling oligonucleotide.

The coupling oligonucleotide can be conjugated to the substrate. The polymer of a substrate can be activated to facilitate conjugation with a polynucleotide or oligonucleotide, such as a coupling oligonucleotide. For example, functional groups on the substrate can be enhanced to permit binding with polynucleotides or oligonucleotides. In a particular example, functional groups of the hydrophilic polymer can be modified with reagents capable of converting the hydrophilic polymer functional groups to reactive moieties that can undergo nucleophilic or electrophilic substitution. For example, hydroxyl groups on the substrate can be activated by replacing at least a portion of the hydroxyl groups with a sulfonate group or chlorine. Exemplary sulfonate groups can be derived from tresyl, mesyl, tosyl, or fosyl chloride, or any combination thereof. Sulfonate can act to permit nucleophiles to replace the sulfonate. The sulfonate may further react with liberated chlorine to provide chlorinated groups that can be used in a process to conjugate the particles. In another example, amine groups on a substrate can be activated.

For example, polynucleotides or oligonucleotides can bind to the hydrophilic polymer through nucleophilic substitution with the sulfonate group. In particular example, polynucleotides or oligonucleotides terminated with a nucleophile, such as an amine or a thiol, can undergo nucleophilic substitution to replace the sulfonate groups on the surface of the substrate.

In another example, sulfonated substrates can be further reacted with mono- or multi-functional mono- or multi-nucleophilic reagents that can form an attachment to the particle while maintaining nucleophilic activity for oligonucleotides comprising electrophilic groups, such as maleimide. In addition, the residual nucleophilic activity can be converted to electrophilic activity by attachment to reagents comprising multi-electrophilic groups, which are subsequently to attach to polynucleotides or oligonucleotides terminated with nucleophilic groups.

In another example, a monomer containing the functional group can be added during the polymerization. The monomer can include, for example, an acrylamide containing a carboxylic acid, ester, halogen or other amine reactive group. The ester group may be hydrolyzed before the reaction with an amine terminated polynucleotide or oligonucleotide.

Other conjugation techniques include the use of monomers that comprise amines. The amine is a nucleophilic group that can be further modified with amine reactive bi-functional bis-electrophilic reagents that yield a monofunctional electrophilic group subsequent to attachment to the substrate. Such an electrophilic group can be reacted with polynucleotides or oligonucleotides having a nucleophilic group, such as an amine or thiol, causing attachment of the oligonucleotide by reaction with the vacant electrophile.

If the substrate is prepared from a combination of amino- and hydroxyl-acrylamides, the substrate can include a combination of nucleophilic amino groups and neutral hydroxyl groups. The amino groups can be modified with di-functional bis-electrophilic moieties, such as a di-isocyanate or bis-NHS ester, resulting in a hydrophilic particle reactive to nucleophiles. An exemplary bis-NHS ester includes bis-succinimidyl C2-C12 alkyl esters, such as bis-succinimidyl suberate or bis-succinimidyl glutarate.

Other activation chemistries include incorporating multiple steps to convert a specified functional group to accommodate specific desired linkages. For example, a sulfonate modified hydroxyl group can be converted into a nucleophilic group through several methods. In an example, reaction of the sulfonate with azide anion yields an azide substituted hydrophilic polymer. The azide can be used directly to conjugate to an acetylene substituted polynucleotide or oligonucleotide via "CLICK" chemistry that can be performed with or without copper catalysis. Optionally, the azide can be converted to amine by, for example, catalytic reduction with hydrogen or reduction with an organic phosphine. The resulting amine can then be converted to an electrophilic group with a variety of reagents, such as di-isocyanates, bis-NHS esters, cyanuric chloride, or a combination thereof. In an example, using di-isocyanates yields a urea linkage between the polymer and a linker that results in a residual isocyanate group that is capable of reacting with an amino substituted polynucleotide or oligonucleotide to yield a urea linkage between the linker and the polynucleotide or oligonucleotide. In another example, using bis-NHS esters yields an amide linkage between the polymer and the linker and a residual NHS ester group that is capable of reacting with an amino substituted polynucleotide or oligonucleotide to yield an amide linkage between the linker and the polynucleotide or oligonucleotide. In a further example, using cyanuric chloride yields an amino-triazine linkage between the polymer and the linker and two residual chloro-triazine groups one of which is capable of reacting with an amino substituted polynucleotide or oligonucleotide to yield an amino-triazine linkage between the linker and the polynucleotide or oligonucleotide. Other nucleophilic groups can be incorporated into the particle via sulfonate activation. For example, reaction of sulfonated particles with thiobenzoic acid anion and hydrolysis of the consequent thiobenzoate incorporates a thiol into the particle which can be subsequently reacted with a maleimide substituted biomolecule to yield a thio-succinimide linkage to the biomolecule. Thiol can also be reacted with a bromo-acetyl group.

Alternatively, acrydite oligonucleotides can be used during the polymerization to incorporate oligonucleotides. An exemplary acrydite oligonucleotide can include an ion-exchanged oligonucleotides.

Returning to FIG. 1, substrates can be incorporated into the amplification solution along with amplification reagents, such as enzymes including polymerase or recombinase, nucleotides (e.g. A, T, C, G, or analogs thereof), various salts or ionic compounds, or a combination thereof. In particular, target polynucleotides, such as polynucleotides derived from biological sources, are included in the amplification solution.

An emulsion is formed that includes the amplification solution as a dispersed phase, as illustrated in 104. In particular, the amplification solution is an aqueous solution and can be dispersed in a hydrophobic phase, such as an oil phase. The hydrophobic phase can include fluorinated liquids, minerals oils, silicone oils, or any combination thereof. Optionally, the hydrophobic phase can include a surfactant, such as a non-ionic surfactant, such as the non-ionic surfactant described below.

The emulsion can be formed utilizing a membrane-based mechanism, in which the aqueous amplification solution and the continuous phase hydrophobic liquid are passed through a membrane one or more times, forming droplets of the amplification solution within the continuous phase hydrophobic liquid. Alternatively, the emulsion can be formed by agitating the amplification solution in the presence of the hydrophobic liquid. In another example, the emulsion can be formed by repeatedly aspirating and ejecting the amplification solution and the hydrophobic continuous phase through a pipette tip. In a further example, droplets of the aqueous amplification solution can be injected into a stream of the hydrophobic liquid.

Following the emulsification of the amplification solution, droplets of amplification solution forming a dispersed phase can include substrates and a target polynucleotide. A portion of the droplets can include one or more substrates and a single target polynucleotide. Other droplets can include substrates and no polynucleotide. Other droplets may include one or more substrates and more than one target polynucleotides.

Figure 2:
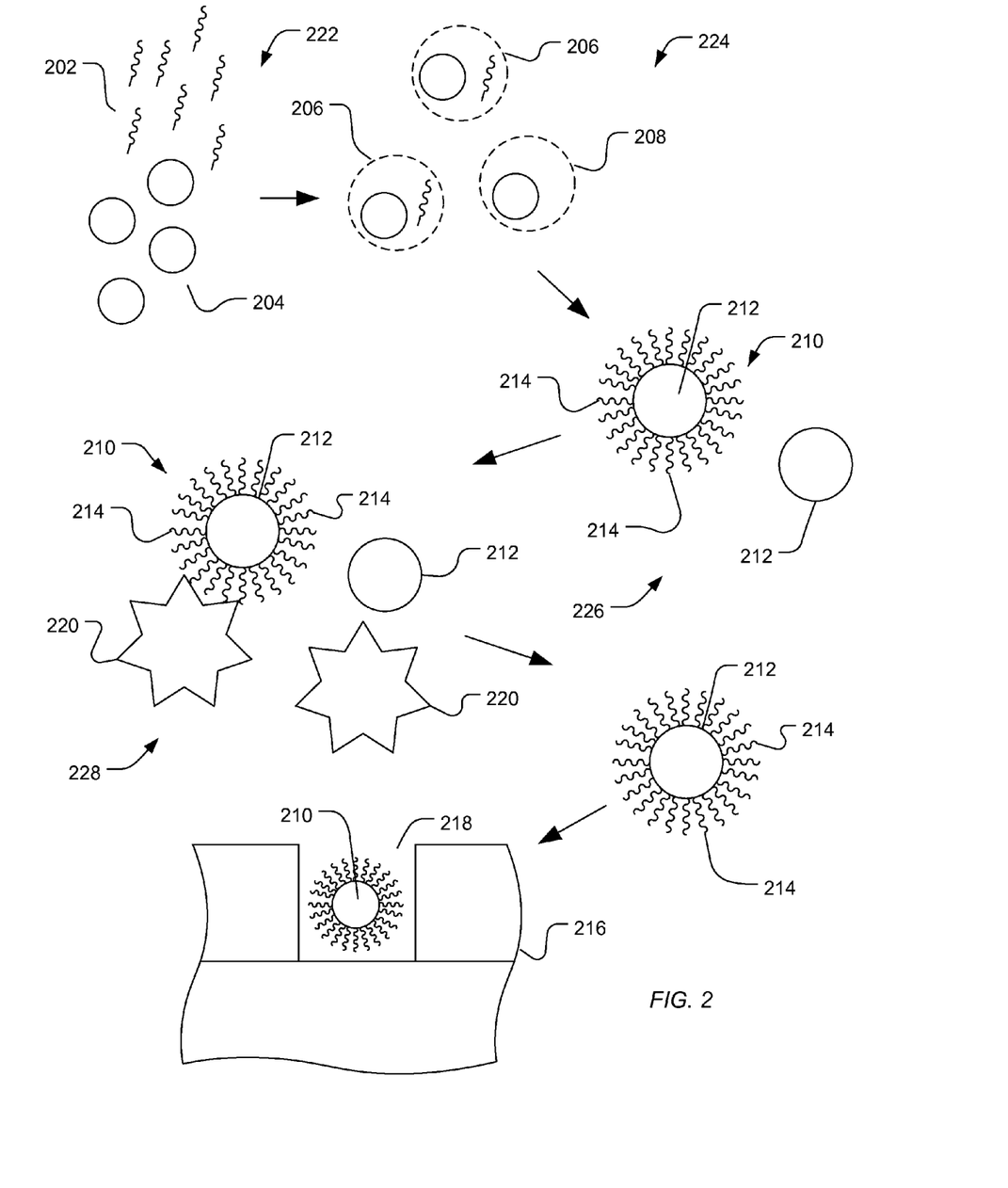
FIG. 2 includes a pictorial illustration of an exemplary method for analyzing a target polynucleotide.

For example, as illustrated in FIG. 2, an aqueous amplification solution 222 includes target polynucleotides 202 and substrates 204. Following emulsification, some droplets 206 of the emulsion 224 can include a single target polynucleotide and one or more substrates. Other droplets 208 of the emulsion 224 can include a substrate and no target polynucleotide.

Returning to FIG. 1, an amplification reaction can be performed to provide amplified substrates, as illustrated at 106. The conditions of the amplification reaction can depend on factors, such as the nature of the enzymes used in the amplification solution, the concentration of individual nucleotides, a concentration of salts or ionic compounds, among other factors. In an example, the amplification reaction is a polymerase chain reaction (PCR) in which the temperature cycles multiple times in a range of 40° C. to 100° C. In another example, the amplification reaction is a recombinase polymerase amplification (RPA). Such reactions can be performed isothermally at a temperature in a range of 40° C. to 90° C. Other amplification techniques can be used, for example, polymerase cycling assembly (PCA), asymmetric PCR, helicase-dependent amplification, ligation-mediated PCR, multiplex-PCR, nanoparticle-assisted PCR, or other amplification techniques.

In an example, during amplification, template polynucleotides including a target sequence of interest and a segment complementary to the coupling oligonucleotide hybridize to the coupling oligonucleotide. The coupling oligonucleotide is extended, forming a complement to the template polynucleotide. The template polynucleotide can further include a capture moiety useful for binding with a separation substrate for later separation of amplified substrates from unamplified substrates.

As a result of the amplification, dispersed phase droplets including target polynucleotides and bead substrates produce amplified substrates including one or more copies of the target polynucleotide conjugated to the substrate. In contrast, droplets including a substrate and lacking a target polynucleotide do not produce substrates that include copies of target polynucleotides and are referred to herein as unamplified substrates.

As illustrated at 108, the emulsion is broken to recover amplified substrates, whereby the liquid of the dispersed phase is separated from the continuous phase. For example, the emulsion may be applied over a breaking solution and optionally agitated or centrifuged. In particular, centrifuging the emulsion through a breaking solution drives substrates into the breaking solution away from an interface between the breaking solution and the continuous phase liquid of the emulsion. The breaking solution can be a hydrophilic liquid, such as an aqueous solution that includes surfactants to assist with augmenting surface tensions and separating the dispersed phase from the continuous phase.

In an example, the breaking solution can include one or more surfactants having a total concentration in the range of 0.01% to 20% by weight. For example, the surfactant can be included in an amount in a range of 0.1% to 15.0%, such as a range of 0.5% to 10.0%, a range of 0.5% to 5.0% or even a range of 0.5% to 3% by weight. In another example, the surfactant can be included in a total amount in a range of 5.0% to 20.0%, such as a range of 10.0% to 20.0%, or a range of 12.0% to 18.0%.

The surfactant can be an ionic surfactant, an amphoteric surfactant, a non-ionic surfactant, or a combination thereof. The ionic surfactant can be an anionic surfactant. An exemplary anionic surfactant includes a sulfate surfactant, a sulfonate surfactant, a phosphate surfactant, a carboxylate surfactant, or any combination thereof. An exemplary sulfate surfactant includes alkyl sulfates, such as ammonium lauryl sulfate, sodium lauryl sulfate (sodium dodecyl sulfate, (SDS)), or a combination thereof; an alkyl ether sulfate, such as sodium laureth sulfate, sodium myreth sulfate, or any combination thereof; or any combination thereof. An exemplary sulfonate surfactant includes an alkyl sulfonate, such as sodium dodecyl sulfonate; docusates such as dioctyl sodium sulfosuccinate; alkyl benzyl sulfonate (e.g., dodecyl benzene sulfonic acid or salts thereof); or any combination thereof. An exemplary phosphate surfactant includes alkyl aryl ether phosphate, alkyl ether phosphate, or any combination thereof. An exemplary carboxylic acid surfactant includes alkyl carboxylates, such as fatty acid salts or sodium stearate; sodium lauroyl sarcosinate; a bile acid salt, such as sodium deoxycholate; or any combination thereof.

In another example, the ionic surfactant can be a cationic surfactant. An exemplary cationic surfactant includes primary, secondary or tertiary amines, quaternary ammonium surfactants, or any combination thereof. An exemplary quaternary ammonium surfactant includes alkyltrimethylammonium salts such as cetyl trimethylammonium bromide (CTAB) or cetyl trimethylammonium chloride (CTAC); cetylpyridinium chloride (CPC); polyethoxylated tallow amine (POEA); benzalkonium chloride (BAC); benzethonium chloride (BZT); 5-bromo-5-nitro-1,3-dioxane; dimethyldioctadecylammonium chloride; dioctadecyldimethylammonium bromide (DODAB); or any combination thereof.

An exemplary amphoteric surfactant includes a primary, secondary, or tertiary amine or a quaternary ammonium cation with a sulfonate, carboxylate, or phosphate anion. An exemplary sulfonate amphoteric surfactant includes (3-[(3-cholamidopropyl)dimethylammonio]-1-propanesulfonate); a sultaine such as cocamidopropyl hydroxysultaine; or any combination thereof. An exemplary carboxylic acid amphoteric surfactant includes amino acids, imino acids, betaines such as cocamidopropyl betaine, or any combination thereof. An exemplary phosphate amphoteric surfactant includes lecithin.

In another example, the surfactant can be a non-ionic surfactant such as a polyethylene glycol-based surfactant, an alkyl pyrrolidine surfactant, an alkyl imidazolidinone surfactant, an alkyl morpholine surfactant, an alkyl imidazole surfactant, an alkyl imidazoline surfactant, or a combination thereof. In a particular example, the polyethylene-glycol-based surfactant includes a polyethylene-glycol ether, such as an alkylphenol polyethoxylate. In another example, the non-ionic surfactant includes a non-ionic fluorosurfactant, such as an ethoxylated fluorocarbon. In a further example, the surfactant solution can include octyl pyrrolidine.

In particular, the surfactant solution can include combinations of such surfactants. For example, the surfactant solution can include a combination of a non-ionic surfactant with an anionic surfactant. In a particular example, the surfactant solution can include a non-ionic surfactant, such as a polyethylene glycol ether, an alkyl pyrrolidine, or a non-ionic fluorosurfactant, and an anionic surfactant, such as a sulfate surfactant, for example SDS. In particular, the surfactant solution can include an ionic surfactant, such as an anionic surfactant, in an amount in a range of 0.1% to 20.0%, such as a range of 1.0% to 15.0%, or a range of 5.0% to 15.0%, or a range of 8.0% to 12.0%. In addition, the surfactant solution can include a non-ionic surfactant, such as alkyl pyrrolidine (e.g., octyl pyrrolidine) in a range of 0.01% to 10.0%, such as a range of 0.05% to 8.0%, or a range of 1.0% to 6.0%. In another example, the surfactant solution can include a non-ionic surfactant in a range of 0.05% to 3.0%.

In a particular example, the emulsion breaking solution includes interference probes, such as oligonucleotides complementary to the coupling oligonucleotide or having a sequence similar to the coupling oligonucleotide. Such an interference probe limits free floating polynucleotides from hybridizing with unamplified substrates.

Referring to FIG. 2, following emulsion breaking, the remaining aqueous solution 226 includes amplified substrates 210. The amplified substrates 210 can include the substrate 212 conjugated to a plurality of copies of the target polynucleotide 214. The solution can also include substrates 212 that do not include copies of target polynucleotides, referred to herein as unamplified substrates.

Returning to FIG. 1, amplified substrates are washed and enriched, as illustrated at 110. In an example, the substrates can be pelletized using centrifugation and excess solution can be decanted or drawn from above the pelletized substrates. In another example, the amplified substrates can be attached to separation substrates used to secure the amplified substrates while the aqueous solution surrounding the amplified substrates is replaced.

For example, as illustrated in FIG. 2, amplified substrates 210 can be captured by a separation substrate 220. In contrast, the unamplified substrates 212 that do not include copies of polynucleotides do not readily attached to the separation substrate 220. Thus, when the separation substrate 220 is secured and the attached amplified substrates 210 are held in place, unsecured unamplified substrates are substantially washed from the solution. In a particular example, the separation substrates 214 are magnetic substrates that can be secured to a container wall using a magnetic field. The amplified substrates 210 can then be separated from the separation substrates 220, providing a solution that has predominantly amplified substrates and substantially fewer unamplified substrates.

In a particular example, the amplified substrates 210 can include a capture moiety that interacts with moieties on the separation substrates 220. The unamplified substrates can be substantially free of the capture moieties. For example, the template polynucleotide can be terminated with a capture moiety. The unamplified substrates not hybridized to a template polynucleotide lack the capture moiety and thus, do not bind with the separation substrate. Once the amplified substrates 210 are separated from the unamplified substrates, the amplified substrates 210 can be separated from the separation substrate, for example, by melting or detaching the template polynucleotide from the extended coupling oligonucleotides conjugated to the amplified substrates 210.

Returning to FIG. 1, the enriched amplified substrates can be loaded onto a biosensor, as illustrated at 112. Depending upon the nature of the biosensor, the biosensor can provide a surface onto which the amplified substrates can be attached. The surface can be flat and optionally can include regions that are more attractive to the amplified substrates or that are modified to secure the amplified substrates. In another example, the biosensor can include a surface that includes discrete sites or patterned surfaces, such as dimples, depressions, pores, wells, ridges or channels into which the amplified substrates align. In a further example, as illustrated in FIG. 2, the biosensor can include a surface structure 216 that defines a well 218 into which the amplified substrates 210 are deposited.

As illustrated at 114 of FIG. 1, the biosensor can sense aspects of the amplified substrate. Depending upon the nature of the biosensor, the sensor can be utilized to detect the presence of particular sequences within the target polynucleotide, or can be used to sequence the target polynucleotide. For example, the biosensor may utilize fluorescence-based sequencing-by-synthesis. In another example, the biosensor can utilize techniques for sequencing that include sensing byproducts of nucleotide incorporation, such as pH or the presence of pyrophosphate or phosphate. In a further example, the biosensor can utilize temperature or heat detection.

Returning to FIG. 2, in an example, a well 218 of an array of wells can be operatively connected to measuring devices. For example, for fluorescent emission methods, a well 218 can be operatively coupled to a light detection device. In the case of ionic detection, the lower surface of the well 218 may be disposed over a sensor pad of an ionic sensor, such as a field effect transistor.

One exemplary system involving sequencing via detection of ionic byproducts of nucleotide incorporation includes semiconductor sequencing platforms, such as an ion-based sequencing system that sequences nucleic acid templates by detecting hydrogen ions produced as a byproduct of nucleotide incorporation. Typically, hydrogen ions are released as byproducts of nucleotide incorporations occurring during template-dependent nucleic acid synthesis by a polymerase. Such a sequencer detects the nucleotide incorporations by detecting the hydrogen ion byproducts of the nucleotide incorporations. Such a sequencer can accommodate a plurality of template polynucleotides or template complements (e.g., extended coupling oligonucleotides) to be sequenced, each template or extended coupling oligonucleotide disposed within a respective sequencing reaction well in an array. The wells of the array can each be coupled to at least one ion sensor that can detect the release of H+ ions or changes in solution pH produced as a byproduct of nucleotide incorporation. The ion sensor comprises a field effect transistor (FET) coupled to an ion-sensitive detection layer that can sense the presence of H+ ions or changes in solution pH. The ion sensor can provide output signals indicative of nucleotide incorporation which can be represented as voltage changes whose magnitude correlates with the H+ ion concentration in a respective well or reaction chamber. Different nucleotide types can be flowed serially into the reaction chamber, and can be incorporated by the polymerase into an extending primer (or polymerization site) in an order determined by the sequence of the template. Each nucleotide incorporation can be accompanied by the release of H+ ions in the reaction well, along with a concomitant change in the localized pH. The release of H+ ions can be registered by the FET of the sensor, which produces signals indicating the occurrence of the nucleotide incorporation. Nucleotides that are not incorporated during a particular nucleotide flow may not produce signals. The amplitude of the signals from the FET can also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers can permit the instrument to resolve the sequence of many nucleic acid templates or extended coupling oligonucleotides simultaneously.

Figure 3:
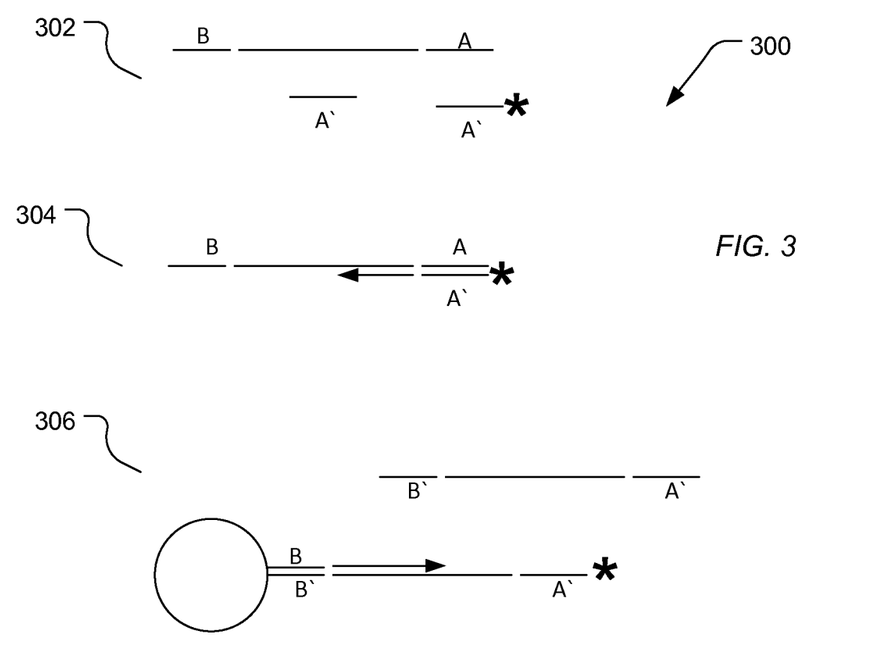
FIG. 3 and FIG. 4 include pictorial illustrations of exemplary methods for amplifying a target polynucleotide.

Optionally during sequencing, a target polynucleotide including an initial segment A separated from a segment B by a target region can be copied utilizing probes complementary to A and optionally including a capture functionality indicated by a "*". For example, as illustrated in FIG. 3, a method 300 includes exposing a target polynucleotide A-B to a set of complementary probes A' and A'*. As illustrated at 304, the target polynucleotide is copied, for example, using the A'* probe resulting in a copy of the target polynucleotide A'-B' that includes the capture functionality (*). The copying can be repeated multiple times using either the A' or A'* primer.

In the example illustrated in FIG. 3, the coupling oligonucleotide conjugated to the substrate can be similar to the B segment of the target polynucleotide and is complementary to the B' segment of the copy of the target polynucleotide. The copies of the target polynucleotide can hybridize to the coupling oligonucleotide of the substrate. The coupling oligonucleotide of the substrate can act as a primer and can be extended to be complementary to the copy of the target polynucleotide, thus including a segment having the same sequence as the target sequence of the target polynucleotide.

While the substrate at 306 is illustrated as including a single coupling oligonucleotide, the substrate can include many copies of the coupling oligonucleotide, such as between 1000 copies and 30 million copies of the coupling oligonucleotide. As such, the substrate can be amplified, i.e., the coupling oligonucleotides B can be extended with copies of the target polynucleotide that include the capture functionality or the capture moiety (*) or that lack the capture functionality. Thus, the amplified substrate can include a number of template copies of the target polynucleotide that are hybridized to the extended coupling oligonucleotide. The substrate can also include extended coupling oligonucleotides hybridized to copies of the target polynucleotide that lack the capture functionality. Alternatively, the extended coupling oligonucleotide can hybridize to an A' or A'* primer.

The coupling oligonucleotide can have a sequence of between 5 and 100 bases, such as between 10 and 50 bases. The B segments can have the same sequence and the same number of bases as the coupling oligonucleotide. The B' segments can have a complementary sequence and the same number of bases as the coupling oligonucleotide. Alternatively, the B or B' segments can have fewer bases and be the same or complementary to at least a portion of the coupling oligonucleotide.

Figure 4:
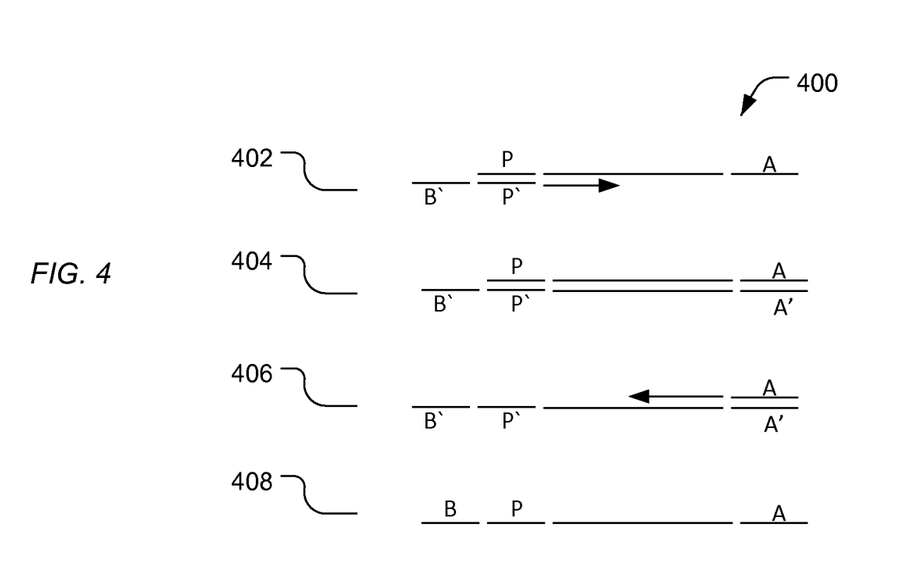

As illustrated in FIG. 4, the target polynucleotide can be generated by providing a polynucleotide having a sequence A coupled via a target sequence to a P segment. As illustrated at 402, and extension probe B'-P' can be hybridized to the segment and the extension probe can be extended. As illustrated at 404, the copy B'P'-A' includes a segment B' that is complementary to the coupling oligonucleotide and a segment that is complementary to the target sequence. As illustrated at 406, an A primer can be applied to the copy B'P'-A' and extended to provide the BP-A target sequence, as illustrated at 408. The BP-A sequence can be used at 302 of FIG. 3 to form the template polynucleotides that hybridize to the coupling oligonucleotide conjugated to the substrate.

Figure 5:
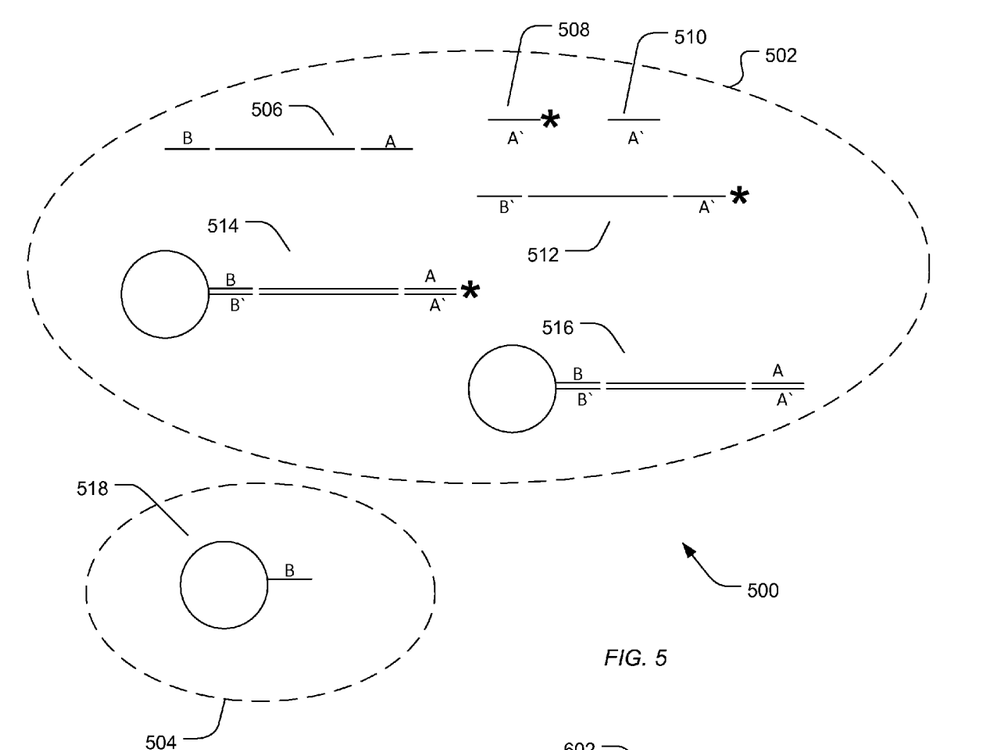
FIG. 5 includes an illustration of an exemplary emulsion.

Turning to FIG. 5, following amplification, the emulsion 500 includes droplets 502 in which amplification reactions can take place. Such droplets 502 can include the target polynucleotide 506, primer sequences A' and A'* (508 or 510) and copies 512 complementary to the target polynucleotide 506 that include the capture functionality (*) or lack the capture functionality. In addition, the amplification reaction takes place in the presence of substrates. The substrates can include reaction sites 514 that include a coupling oligonucleotide extended by hybridizing the coupling oligonucleotide to a template polynucleotide that includes the capture functionality or reaction sites 516 including the extended coupling oligonucleotide hybridized to template polynucleotides that lack the capture functionality. The droplets 502 can also include free-floating nucleotides, enzymes, and various ionic compounds. Further, the extended coupling oligonucleotide can hybridize to A' or A'* primers.

In addition, the emulsion 500 can include droplets 504 that include substrates and lack a target polynucleotide. As a result of the application, substrates 518 include the coupling oligonucleotide that has not been extended and is not hybridized to complements to the target polynucleotide. However, in response to breaking of emulsion, such unamplified substrates 518 can hybridize to free-floating complements 512 of the target polynucleotide. As illustrated at 602 of FIG. 6, such hybridization can result in unamplified substrates 518 including the capture functionality and thus having the ability to attach to separation substrates, preventing such unamplified substrates from being washed out of the solution and competing for separation substrates with the amplified substrates.

Figure 6:
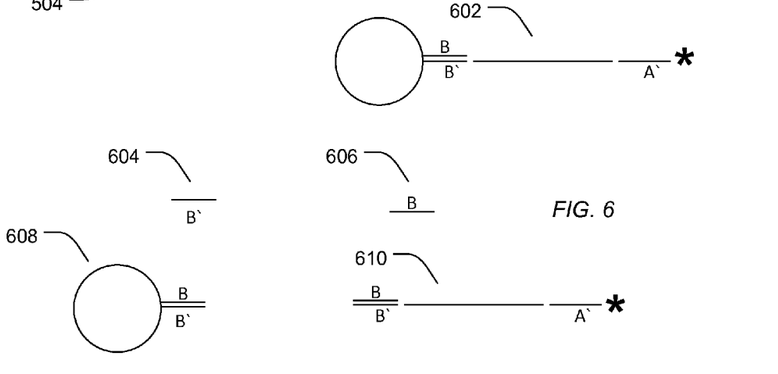
FIG. 6 includes a pictorial illustration of exemplary byproducts following emulsion amplification.

The emulsion breaking solution can include an interference probe B' (604) complementary to the coupling oligonucleotide, can include an interference probe B (606) having at least a portion of the sequence similar to the coupling oligonucleotide, or can include both. In a particular example, the emulsion breaking solution can include the interference probe B (606). The interference probe 604 is complementary to the coupling oligonucleotide and can attached to unamplified coupling oligonucleotides on a substrate 608 and prevent subsequent binding of free-floating complements of the target polynucleotide. In another example, the probe 606 includes a segment similar to the coupling oligonucleotide that can bind with the free-floating complements of the target polynucleotide 610 and prevent them from hybridizing with coupling oligonucleotide sites, such as those on unamplified substrates. Such probes 604 and 606 compete with the free-floating complements to the target polynucleotide and the unextended coupling oligonucleotides on the unamplified substrates to limit the unamplified substrates from acquiring capture functionality.

Figure 7:
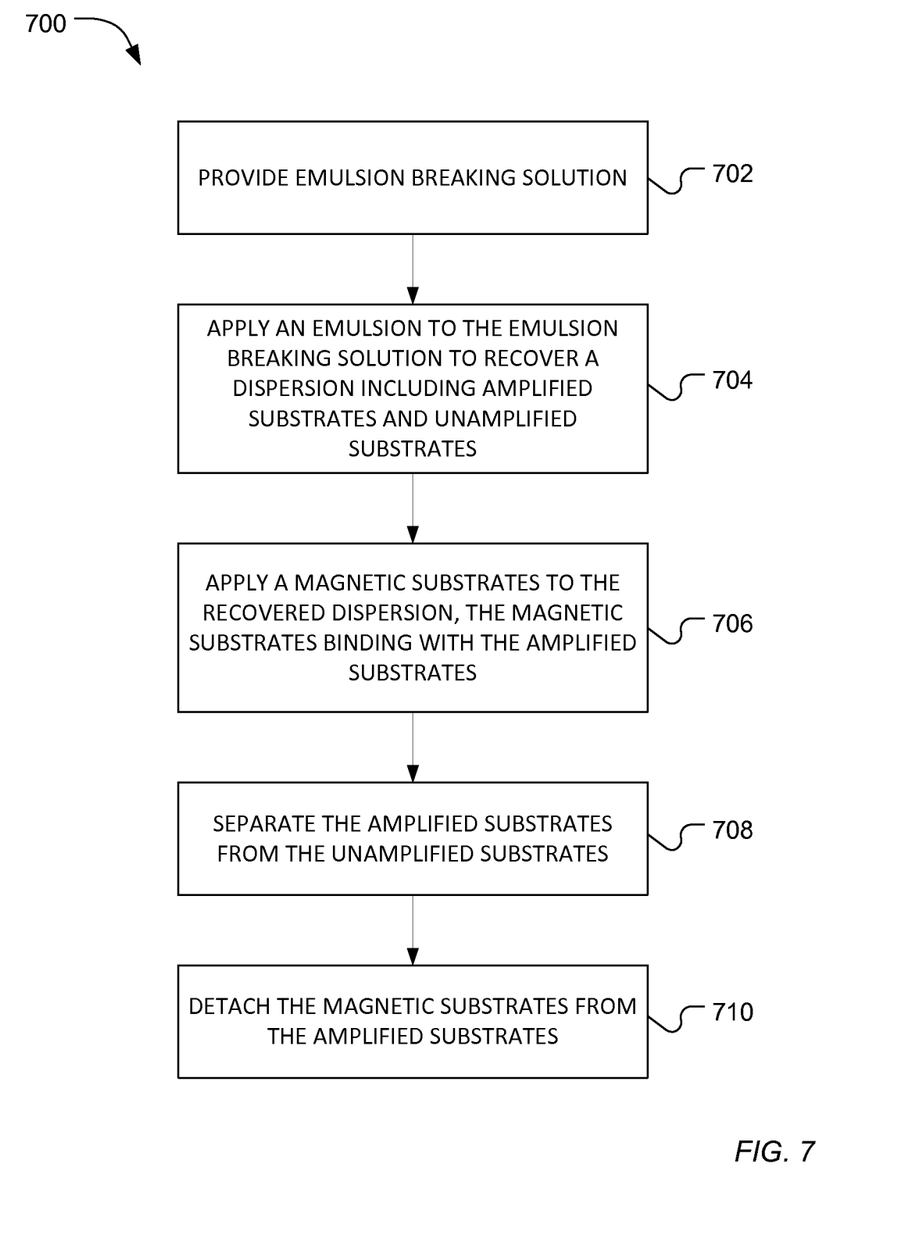
FIG. 7 includes a block flow diagram illustrating an exemplary method for enriching dispersed substrates.

In a particular example, the amplified substrates are enriched, separating the amplified substrates from the unamplified substrates using a magnetic separation technique. For example, as illustrated in FIG. 7, a method 700 includes providing an emulsion breaking solution, as illustrated at 702. The emulsion breaking solution can include surfactants. In particular, the emulsion breaking solution includes interference probes complementary to the coupling oligonucleotides on the substrates or having the same sequence as the coupling oligonucleotides and complementary to segments of the complements to the target polynucleotide. In an example, the emulsion breaking solution has a composition similar to that described above.

An emulsion is applied to the emulsion breaking solution to recover a dispersion including the amplified substrates and unamplified substrates, as illustrated at 704. The interference probes can interfere with the binding interaction of free-floating complements to the target polynucleotides and the unamplified coupling oligonucleotides of unamplified substrates.

In particular, the capture functionality can include a component of a pair that permits binding of the capture functionality to an associated capture functionality on the separation substrate. For example, the capture functionality can be one of biotin or an avidin derivative such as streptavidin. In such an example, substrates including extended binding sites that are hybridized to polynucleotides including the capture functionality, such as biotin, can bind to a magnetic substrate that includes an opposite capturing functionality, such as streptavidin. In another example, the capture functionality can include CLICK chemistry.

As illustrated at 706, a magnetic substrate can be applied to the recovered dispersion. The magnetic substrates can bind with the amplified substrates by virtue of coupling sites or coupling oligonucleotides being hybridized to polynucleotides including capture functionality or to any A$^{1*}$ primer in solution. As a result of the competing behavior with the interference probes, few, if any, unamplified substrates hybridize to the polynucleotides having capture functionality. Thus, the unamplified substrates are limited from binding to the magnetic substrates. In a particular example, the magnetic substrates can be magnetic polystyrene substrates including streptavidin functionality.

The amplified substrates can be separated from the unamplified substrates, as illustrated at 706. In particular, a magnetic field may be applied to a container, drawing the magnetic substrates that are coupled to the amplified substrates into contact with the wall and securing the amplified substrates and magnetic substrates within the container. The solution can then be washed and replaced one or more times resulting in a flushing of components and substrates (e.g., the unamplified substrates) not secured by the magnetic substrates.

Following separation of the amplified substrates from the unamplified substrates, the amplified substrates can be detached from the magnetic substrates, as illustrated at 710. In a particular example, the template polynucleotides that are hybridized to the amplified substrates can be melted or otherwise separated from the extended coupling oligonucleotides. Such melting or separation can be accomplished using a change in ionic concentration, can be accomplished using a change in temperature, or a combination thereof. As such, the magnetic substrates secured within the container retain the captured template polynucleotide having the capture functionality, while the amplified substrates are dispersed within solution and separated from the magnetic substrates.

Figure 8:
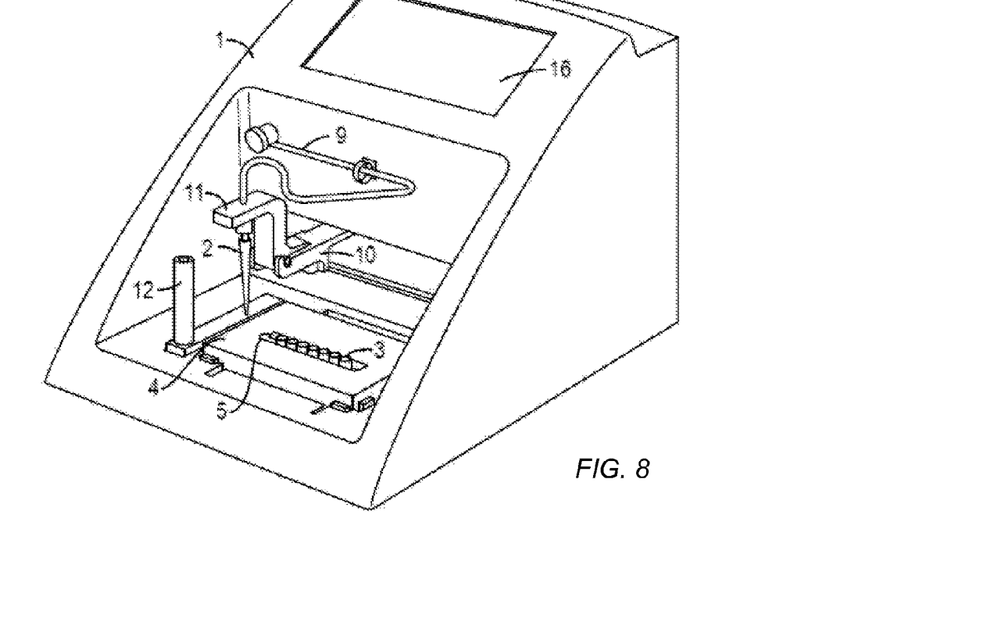
FIG. 8 and FIG. 9 include illustrations of exemplary devices for enriching dispersed substrates.
Figure 9:
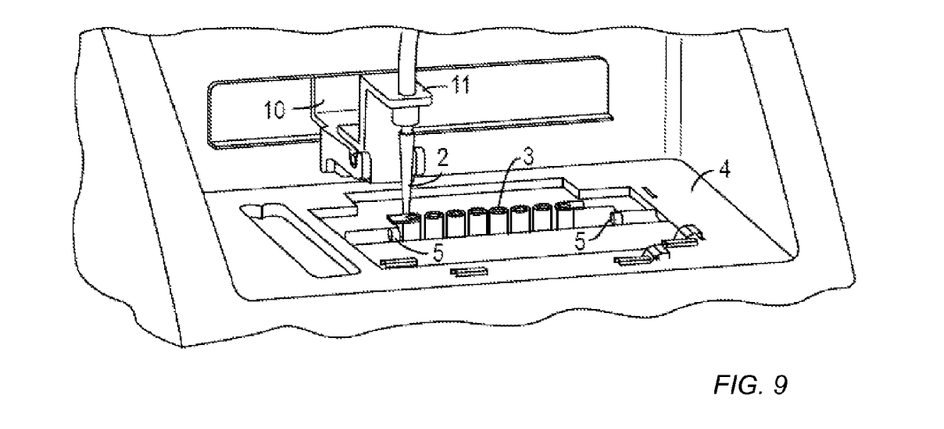

The method 700 illustrated in FIG. 7 can be automated using an automated sample handling device as illustrated in FIG. 8 and FIG. 9. An exemplary device includes a platform 4 holding an X×Y array 3 (illustrated as a onexeight strip) preloaded with a magnetic fraction sample to be separated and any reagents/solutions/material used in the automated process. The device can also include an arm (e.g., a mechanical stage or arm) 11 for holding a pipette 2, and a tubing port 12 for detachable connection to a pump (not pictured) via tubing 9. The mechanical stage or arm may be detachably connected to a cradle 10 and may form a hinged joint therebetween. The mechanical stage or arm may be adapted to use the pipette to engage the array 3 to position the sample in an IN or an OUT position such that the sample at a separation site is either within a magnetic field, for example, formed by magnet 5, or is sufficiently distant so as not to affect the magnetic fraction in the sample at the separation site, respectively.

The device can further include a receptacle for a container to which a processed sample may be transferred. For example, the container may be a tube (e.g., a PCR tube). The receptacle may be placed at any suitable location in the apparatus as long as it can be reached by the device mounted on the mechanical stage. In some embodiments, the receptacle and the container is disposed next to the holder for holding the device.

In various embodiments, the method can be carried out as follows using a two dimensional array with X by Y number of sites, where X corresponds to the number of samples to be manipulated by one automated process and where Y number of sites is 8. Embodiments of the automated sample handling device may be particularly well suited for performing the following method. Positions of the array of wells are referenced herein using alphabetic identifiers A, B, C, D, E, F, G, or H, in which adjacent wells have consecutive alphabetic identifiers. The apparatus can perform the following sample manipulation sequence: 1) moving tip to Y position B then mixing solution via multiple aspirate/dispense cycles, 2) aspirating then transferring solution to Y position A, 3) mixing solutions at Y position A via multiple aspirate/dispense cycles, 4) actuating magnet, then aspirating and transferring solution to Y position G wells (fail safe), 5) returning tip array to position A, 6) de-actuating magnet, 7) dispensing wash solution and mix via multiple aspirate/dispense cycles, 8) actuating magnet then aspirating solution to waste reservoir, 9) repeating wash cycle as in steps 6, 7 and 8, 10) moving tip Y position F and aspirating, then transferring solution to Y position A wells, and 11) de-actuating magnet and mixing solution via multiple aspirate/dispense cycles and transferring the solution to Y position H.

After the above steps, the user collects the processed sample in Y position H. Alternatively, a method can be implemented using a sample tube, a reagent well, and a disposal container in contrast to an eight position array.

As described above, the enriched amplified substrates can be loaded into a biosensor for determining characteristics of the amplified substrates. In particular, the enriched amplified substrates can be used for sequence target sequences conjugated to the amplified substrates. For example, sequencing can include label-free DNA sequencing, and in particular, pH-based DNA sequencing. Substrates including DNA templates and having a primer and polymerase operably bound are loaded into reaction chambers (such as microwells), after which repeated cycles of deoxynucleoside triphosphate (dNTP) addition and washing are carried out. Such templates are typically attached as clonal populations to the substrate, such as a microparticle, bead, or the like, and such clonal populations are loaded into reaction chambers. In each addition step of the cycle, the polymerase extends the primer by incorporating added dNTP when the next base in the template is the complement of the added dNTP. When there is one complementary base, there is one incorporation, when two, there are two incorporations, when three, there are three incorporations, and so on. With each such incorporation there is a hydrogen ion released, and collectively a population of templates releasing hydrogen ions causing very slight changes the local pH of the reaction chamber which is detected by an electronic sensor.

Figure 10:
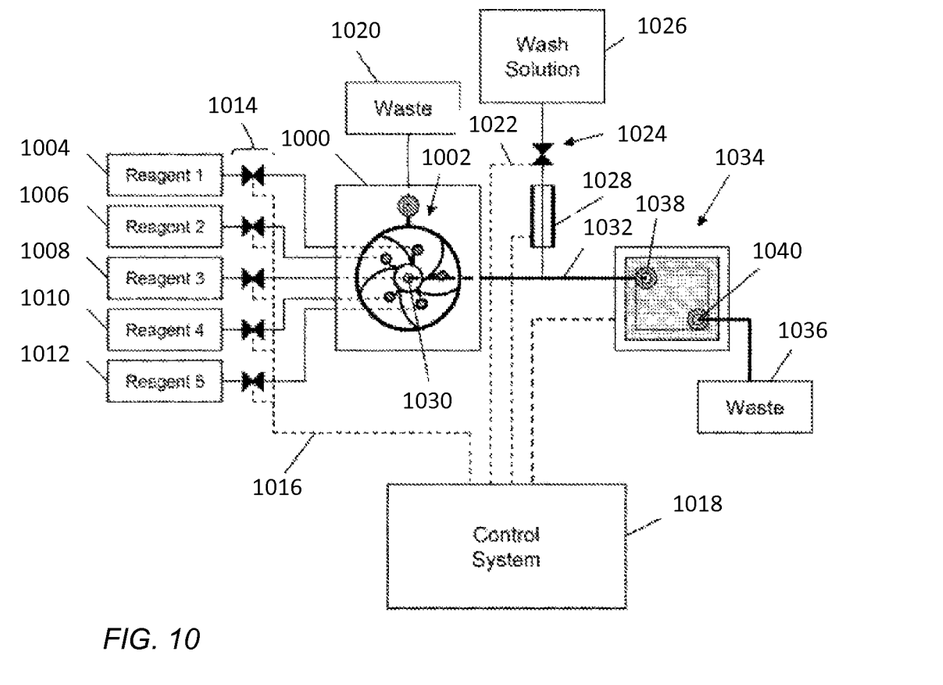
FIG. 10 includes an illustration of exemplary system for sequencing.

FIG. 10 diagrammatically illustrates an apparatus for carrying out pH-based nucleic acid sequencing. Each electronic sensor of the apparatus generates an output signal that depends on the value of a reference voltage. In FIG. 10, housing (1000) containing fluidics circuit (1002) is connected by inlets to reagent reservoirs (1004, 1006, 1008, 1010, and 1012), to waste reservoir (1020) and to flow cell (1034) by passage (1032) that connects fluidics node (1030) to inlet (1038) of flow cell (1034). Reagents from reservoirs (1004, 1006, 1008, 1010, and 1012) may be driven to fluidic circuit (1002) by a variety of methods including pressure, pumps, such as syringe pumps, gravity feed, and the like, and are selected by control of valves (1014). Control system (1018) includes controllers for valves (1014) that generate signals for opening and closing via electrical connection (1016). Control system (1018) also includes controllers for other components of the system, such as wash solution valve (1024) connected thereto by (1022), and reference electrode (1028). Control system (1018) may also include control and data acquisition functions for flow cell (1034). In one mode of operation, fluidic circuit (1002) delivers a sequence of selected reagents (1, 2, 3, 4, or 5) to flow cell (1034) under programmed control of control system (1018), such that in between selected reagent flows fluidics circuit (1002) is primed and washed, and flow cell (1034) is washed. Fluids entering flow cell (1034) exit through outlet (1040) and are deposited in waste container (1036). Throughout such an operation, the reactions or measurements taking place in flow cell (1034) have a stable reference voltage because reference electrode (1028) has a continuous, i.e. uninterrupted, electrolyte pathway with flow cell (1034), but is in physical contact with only the wash solution.

EXAMPLE 1

Following emulsion amplification, an emulsion is applied over 300 microliters of one of four sample breaking solutions. The sample breaking solutions include 10% SDS, 1% octyl-pyrrolidone, and optionally 16 uM B primer, 32 uM B primer, or 32 uM B' primer. Substrates recovered from the emulsion are separated using a magnetic separation technique. As illustrated in Table 1, those breaking solutions that included an interference probe (B primer or B' primer) exhibited increased enriched percentage, the percentage of recovered substrates that are amplified.

TABLE 1

Enrichment of Substrates

| Primer | Avg. Enrichment Percentage |
|---|---|
| 0 uM | 77.25 |
| 16 uM B primer | 90 |
| 32 uM B primer | 93.3 |
| 32 uM B' primer | 93.9 |

EXAMPLE 2

Following emulsion amplification, an emulsion is applied over 300 microliters of one of four sample breaking solutions. The sample breaking solutions include 10% SDS, 1% octyl-pyrrolidone, and optionally B primer in concentrations of 1.6 uM, 3.2 uM, 6.4 uM, 16 uM, or 32 uM. Substrates recovered from the emulsion are separated using a magnetic separation technique. As illustrated in Table 2, those breaking solutions that included an interference probe (B primer) exhibited increased enriched percentage, the percentage of recovered substrates that are amplified.

TABLE 2

Enrichment of Substrates

| uM B Primer | Avg. Enrichment Percentage |
|---|---|
| 1.6 | 93.5 |
| 3.2 | 94.05 |
| 6.4 | 96.15 |
| 16 | 98.5 |
| 32 | 97.95 |

In a first aspect, a method of separating bead substrates includes applying an emulsion to an emulsion-breaking solution. A dispersed phase of the emulsion includes an unbound polynucleotide, a first set of bead substrates and a second set of bead substrates. The unbound polynucleotide includes a segment complementary to a coupling oligonucleotide. The first set of bead substrates includes the coupling oligonucleotide extended to include a segment complementary to a portion of the unbound polynucleotide. The second set of bead substrates includes the coupling oligonucleotide. The emulsion-breaking solution includes an interference probe having a sequence similar to the coupling oligonucleotide or complementary to the coupling oligonucleotide. The method further includes binding beads of the first set of bead substrates to separation substrates and separating unbound beads of the second set of bead substrates from the beads of the first set of bead substrates bound to the separation substrates.

In an example of the first aspect, the interference probe has the sequence similar to the coupling oligonucleotide.

In another example of the first aspect and the above examples, the interference probe has a sequence complementary to the coupling oligonucleotide.

In a further example of the first aspect and the above examples, beads of the second set of bead substrates are substantially free of extension to the coupling oligonucleotide.

In an additional example of the first aspect and the above examples, the unbound polynucleotide includes a capture functionality. In an example, the extended coupling oligonucleotide of the first set of bead substrates is hybridized to a polynucleotide including the capture functionality. For example, the coupling functionality includes biotin. In a further example, the separation substrates include functionality to attach to the capture functionality.

In another example of the first aspect and the above examples, the separation substrates include magnetic beads. For example, the method further includes, prior to separating the unbound beads of the second set of bead substrates, immobilizing with a magnet the magnetic beads bound to beads of the first set of bead substrates.

In a further example of the first aspect and the above examples, the emulsion-breaking solution includes a surfactant. For example, the surfactant includes a non-ionic surfactant. In another example, the surfactant includes an ionic surfactant. For example, the ionic surfactant is an anionic surfactant.

In a second aspect, a method of separating bead substrates includes applying an emulsion to an emulsion-breaking solution. A dispersed phase of the emulsion comprising an unbound polynucleotide, a first set of bead substrates and a second set of bead substrates. The unbound polynucleotide includes a first segment complementary to a coupling oligonucleotide and a second segment attached to a capture functionality. The first set of bead substrates includes the coupling oligonucleotide hybridized to a polynucleotide including the first segment complementary to the coupling nucleotide and the second segment attached to the capture functionality. The second set of bead substrates including the coupling oligonucleotide substantially not hybridized to the polynucleotide or the unbound polynucleotide. The emulsion-breaking solution includes an interference probe having a sequence similar to the coupling oligonucleotide or complementary to the coupling oligonucleotide. The method further includes binding beads of the first set of bead substrates to separation substrates, the separation substrates including functionality to attach to the capture functionality and separating unbound beads of the second set of bead substrates from the bound beads of the first set of bead substrates.

In an example of the second aspect, the interference probe has the sequence similar to the coupling oligonucleotide.

In another example of the second aspect, the interference probe has a sequence complementary to the coupling oligonucleotide.

In a further example of the second aspect and the above examples, the coupling functionality includes biotin. For example, the functionality to attach to the capture functionality includes streptavidin.

In an additional example of the second aspect and the above examples, the separation substrates include magnetic beads. For example, the method further includes, prior to separating the unbound beads of the second set of bead substrates, immobilizing with a magnet the magnetic beads bound to beads of the first set of bead substrates.

In another example of the second aspect and the above examples, the emulsion-breaking solution includes a surfactant. For example, the surfactant includes a non-ionic surfactant. In another example, the surfactant includes an ionic surfactant. For example, the ionic surfactant is an anionic surfactant.

In a third aspect, a kit includes a dispersion of substrates conjugated to coupling oligonucleotides and an emulsion breaking solution including a surfactant and an interference probe, the interference probe having a sequence similar to the coupling oligonucleotide or having a sequence complementary to the coupling oligonucleotide.

In an example of the third aspect, the surfactant includes a non-ionic surfactant.

In another example of the third aspect, the surfactant includes an ionic surfactant. For example, the ionic surfactant is an anionic surfactant.

In a further example of the third aspect and the above examples, the interference probe has a sequence similar to the coupling oligonucleotide.

In an additional example of the third aspect and the above examples, the interference probe has a sequence complementary to the coupling oligonucleotide.

In another example of the third aspect and the above examples, the kit further includes a hydrophobic liquid for forming a continuous phase of an emulsion.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method of separating bead substrates, the method comprising:
    applying an emulsion to an emulsion-breaking solution, the emulsion breaking solution being an aqueous solution including a surfactant, a dispersed phase of the emulsion comprising an unbound polynucleotide, a first set of bead substrates and a second set of bead substrates, the unbound polynucleotide including a segment complementary to a coupling oligonucleotide, the first set of bead substrates including the coupling oligonucleotide extended to include a segment complementary to a portion of the unbound polynucleotide, the second set of bead substrates including the coupling oligonucleotide, the emulsion-breaking solution including an interference probe having a sequence the same as at least a portion of the coupling oligonucleotide or complementary to the coupling oligonucleotide;
    binding beads of the first set of bead substrates to separation substrates; and
    separating unbound beads of the second set of bead substrates from the beads of the first set of bead substrates bound to the separation substrates.

2. The method of claim 1, wherein the interference probe has the sequence the same as at least a portion of the coupling oligonucleotide.

3. The method of claim 1, wherein the interference probe has a sequence complementary to the coupling oligonucleotide.

4. The method of claim 1, wherein beads of the second set of bead substrates are free of extension to the coupling oligonucleotide.

5. The method of claim 1, wherein the unbound polynucleotide includes a capture functionality.

6. The method of claim 5, wherein the extended coupling oligonucleotide of the first set of bead substrates is hybridized to a polynucleotide including the capture functionality.

7. The method of claim 6, wherein the coupling functionality includes biotin.

8. The method of claim 6, wherein the separation substrates include functionality to attach to the capture functionality.

9. The method of claim 1, wherein the separation substrates include magnetic beads.

10. The method of claim 9, further comprising, prior to separating the unbound beads of the second set of bead substrates, immobilizing with a magnet the magnetic beads bound to beads of the first set of bead substrates.

11. The method of claim 1, wherein the surfactant includes a non-ionic surfactant.

12. The method of claim 1, wherein the surfactant includes an ionic surfactant.

13. The method of claim 12, wherein the ionic surfactant is an anionic surfactant.

14. A method of separating bead substrates, the method comprising:
    applying an emulsion to an emulsion-breaking solution, the emulsion breaking solution being an aqueous solution including a surfactant, a dispersed phase of the emulsion comprising an unbound polynucleotide, a first set of bead substrates and a second set of bead substrates, the unbound polynucleotide including a first segment complementary to a coupling oligonucleotide and a second segment attached to a capture functionality, the first set of bead substrates including the coupling oligonucleotide hybridized to a polynucleotide including the first segment complementary to the coupling nucleotide and the second segment attached to the capture functionality, the second set of bead substrates including the coupling oligonucleotide not hybridized to the polynucleotide or the unbound polynucleotide, the emulsion-breaking solution including an interference probe having a sequence to hybridize with complements of the coupling oligonucleotide or complementary to the coupling oligonucleotide;
    binding beads of the first set of bead substrates to separation substrates, the separation substrates including functionality to attach to the capture functionality; and
    separating unbound beads of the second set of bead substrates from the bound beads of the first set of bead substrates.

15. The method of claim 14, wherein the interference probe has the sequence to hybridize with complements of the coupling oligonucleotide.

16. The method of claim 14, wherein the interference probe has a sequence complementary to the coupling oligonucleotide.

17. The method of claim 14, wherein the coupling functionality includes biotin and the functionality to attach to the capture functionality includes streptavidin.

18. The method of claim 14, wherein the separation substrates include magnetic beads.

19. The method of claim 18, further comprising, prior to separating the unbound beads of the second set of bead substrates, immobilizing with a magnet the magnetic beads bound to beads of the first set of bead substrates.

* * * * *

UNITED STATES PATENT AND TRADEMARK OFFICE
CERTIFICATE OF CORRECTION

PATENT NO. : 9,534,215 B2
APPLICATION NO. : 14/736734
DATED : January 3, 2017
INVENTOR(S) : Brian Reed It is certified that error appears in the above-identified patent and that said Letters Patent is hereby corrected as shown below:

In the Specification

In Column 1, Line 8, please replace "61/010,573" with --62/010,573--.

Signed and Sealed this
Twenty-fifth Day of April, 2017

Michelle K. Lee
*Director of the United States Patent and Trademark Office*